United States Patent [19]
Bymaster et al.

[11] Patent Number: 5,980,933
[45] Date of Patent: *Nov. 9, 1999

[54] TRANSDERMAL FORMULATION OF XANOMELINE

[75] Inventors: Franklin Porter Bymaster, Brownburg, Ind.; Michael Horstmann, Neuwied, Germany; Harlan E. Shannon, Carmel; Lisa A. Shipley, Fishers, both of Ind.; Kirti H. Valia, Plainsburo, N.J.

[73] Assignee: Eli Liily and Company, Indianapolis, Ind.

[ * ] Notice: This patent issued on a continued prosecution application filed under 37 CFR 1.53(d), and is subject to the twenty year patent term provisions of 35 U.S.C. 154(a)(2).

[21] Appl. No.: 08/942,141

[22] Filed: Sep. 29, 1997

Related U.S. Application Data

[63] Continuation of application No. 08/778,438, Jan. 2, 1997, abandoned, which is a continuation of application No. 08/380,478, Jan. 30, 1995, abandoned.

[51] Int. Cl.$^6$ ...................................................... A61F 13/02
[52] U.S. Cl. ........................................... 424/448; 424/449
[58] Field of Search ...................................... 424/448, 449

[56] References Cited

U.S. PATENT DOCUMENTS

| | | | |
|---|---|---|---|
| 4,316,893 | 2/1982 | Rajadhyaksha | 424/180 |
| 4,908,027 | 3/1990 | Enscore et al. | 604/890.1 |
| 5,043,345 | 8/1991 | Sauerberg et al. | 514/342 |
| 5,089,267 | 2/1992 | Hille et al. | 424/449 |
| 5,130,319 | 7/1992 | Pinza et al. | 514/300 |
| 5,238,933 | 8/1993 | Catz et al. | 514/236.2 |
| 5,260,314 | 11/1993 | Sauerberg et al. | 514/305 |
| 5,344,656 | 9/1994 | Enscore et al. | 424/448 |

FOREIGN PATENT DOCUMENTS

| | | | |
|---|---|---|---|
| 0 271 983 | 6/1988 | European Pat. Off. . | |
| 0 306 192 | 3/1989 | European Pat. Off. . | |
| 0 384 285 | 8/1990 | European Pat. Off. | 413/4 |
| 0 384 288 | 8/1990 | European Pat. Off. | 417/4 |
| 0 484 186 | 6/1992 | European Pat. Off. | 31/44 |

*Primary Examiner*—D. Gabrielle Brouillette
*Attorney, Agent, or Firm*—Arleen Palmberg

[57] ABSTRACT

The present invention provides a method for treating Alzheimer's Disease using a xanomeline transdermal formulation. The invention provides desired transdermal xanomeline patch formulations.

20 Claims, No Drawings

TRANSDERMAL FORMULATION OF XANOMELINE

This application is a continuation of application Ser. No. 08/778,438, filed on Jan. 2, 1997, now abandoned, which in turn is a continuation of application Ser. No. 08/380,478, filed on Jan. 30, 1995, now abandoned.

FIELD OF THE INVENTION

The present invention provides a novel transdermal formulation containing the pharmaceutically active compound 3-[4-(hexyloxy)-1,2,5-thiadiazol-3-yl]-1,2,5,6-tetrahydro-1-methylpyridine (xanomeline).

BACKGROUND OF THE INVENTION

Xanomeline, described in U.S. Pat. No. 5,043,345 ('345), is a compound having muscarinic activity which can be useful for the treatment of Alzheimer's Disease. As set forth in the '315 patent, xanomeline can be prepared in a solid form for oral use, in the form of suppositories for rectal administration, or in the form of sterile injectable solutions for parenteral use. A formulation for a typical tablet is provided; however, the patent does not suggest that it would be possible or desirable to prepare a transdermal xanomeline patch formulation.

Applicants have discovered that the transdermal xanomeline patch formulation of this invention provides suprising beneficial effects. The present invention provides a method for treating Alzheimer's disease with fewer side effects than are typically associated with muscarinic agonists like xanomeline.

The transdermal formulation of this invention provides consistent dosage of the active ingredient, achieves sustained plasma concentration of the pharmaceutically active agent, and encourages patient compliance.

SUMMARY OF THE INVENTION

The present invention provides a transdermal xanomeline patch formulation comprising an effective amount of xanomeline, from 0.1 to 10 parts by weight azone, from 30 to 69.8 parts ethanol, 29 to 50 parts by weight water, from 0 to 30 parts by weight propylene glycol, and 1 to 5 parts by weight Klucel HF.

Further, there is provided a transdermal xanomeline patch formulation comprising an effective amount of xanomeline and from about 70 to 99.8% acrylate adhesive. There is provided a transdermal patch wherein xanomeline is intimately distributed in a matrix.

Additionally, there is provided a transdermal xanomeline patch formulation comprising an effective amount of xanomeline, from 85 to 97 parts by weight ethanol and from 2 to 14.9 parts Klucel HF.

Finally, there is provided a method for treating Alzheimer's disease comprising administering xanomeline transdermally using a patch formulation.

DETAILED DESCRIPTION OF THE INVENTION

As used herein "xanomeline" shall refer to the free base, a pharmaceutically acceptable salt or solvate thereof. The free base is preferred. The transdermal xanomeline patch formulations of the present invention provide surprising beneficial properties. The xanomeline tablet was associated with undesired parasympathomimetic effects when administered to humans. Applicants have discovered that the transdermal patch formulation can minimize such effects while providing higher sustained plasma levels of the pharmaceutically active agent.

Although the transdermal patch formulations claimed herein are preferred for the transdermal delivery of xanomeline, other transdermal formulations may be employed. Percutaneous or transdermal delivery of pharmacologically active agents has become feasible in recent years largely due to vehicles therefor which allow increased permeation of said agents into the body surface to which applied. Such agents which may be useful for the preparation of a xanomeline transdermal patch formulation include, but are not necessarily limited to, dimethylsulfoxide (U.S. Pat. No. 3,551,554); various 1-substituted azacycloalkan-2-ones such as azone (U.S. Pat. Nos. 4,562,075, 4,405,616, 4,326,893 and 3,989,816); sugar esters in combination with sulfoxide or phosphine oxide (U.S. Pat. Nos. 4,130,667, 4,130,643, 4,046,886, 3,952,099, and 3,896,238); lower alkyl amides (U.S. Pat. No. 3,472,931); certain aliphatic sulfoxides (U.S. Pat. No. 3,903,256); a composition containing glycerol monooleate, ethanol and isopropyl myristate (U.S. Pat. No. 4,335,115); a binary mixture of 1-dodecylazacycloheptan-2-one and a compound selected from a diol or a second N-substituted azacycloalkyl-2-one (U.S. Pat. No. 4,557,934); and polyethylene glycol monolaurate (U.S. Pat. No. 4,568,343). U.S. Pat. Nos. 3,551,554, 4,562,075, 4,405,616, 4,326,893, 3,989,816, 4,130,667, 4,130,643, 4,046,886, 3,952,099, 3,896,238, 3,472,931, 3,903,256, 4,335,115, 4,557,934, and 4,568,343 are hereby incorporated by reference in their entirety.

It is contemplated that the transdermal patch formulations of this invention will find utility in both humans and animals, i.e., will have both medical and veterinary applications for providing increased percutaneous absorption of the pharmaceutically active agent. As used herein, the term "percutaneous" refers to the passage of such agents through skin (typically intact).

The transdermal formulations of the present invention may be administered using a variety of devices which have been described in the art. For example, such devices include, but are not limited to those described in U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, and 4,292,303 each of which is hereby incorporated by reference in its entirety. The dosage forms of the present invention may incorporate certain pharmaceutically acceptable excipients which are conventional in the art. These include, but are not limited to, gelling agents, cream and ointment bases, and the like.

Xanomeline shall be present in the claimed dosage forms in an effective amount. The term "an effective amount" shall refer to an amount calculated to achieve and maintain blood levels which will bring about the desired beneficial or therapeutic effect over the period of time desired. These amounts will vary depending the amount of pharmacologically active agent required to achieve the desired beneficial or therapeutic effect, whether one or more patches will be administered simultaneously the specific formulation of the patch, the age and condition of the patient to be treated, and the like. Such conventional dosage titration techniques, familiar to the skilled artisan, may be utilized to determine the amount of xanomeline present in the ultimate pharmaceutical dosage form for any specific situation.

The pharmacologically active xanomeline is administered by known techniques such as placing the patch containing said agent and transdermal formulation therefor on a body surface and maintaining said source on said body surface in agent and composition transmitting relation thereto.

One of the transdermal xanomeline patch formulations utilizes ethanol, water, azone, and optionally propylene glycol to enhance the permeation of the pharmacologically active xanomeline. As noted supra., azone is known to be useful for transdermal permeation enhancement and is chemically 1-dodecylazacyloheptan-2-one. Azone can be prepared as described in U.S. Pat. No. 4,316,893, hereby incorporated by reference.

Formulation of the claimed compositions may be achieved by conventional methods, as by the simple mixing of all components thoroughly. The artisan will appreciate that compositions containing diols other than propylene glycol and alcohols other than ethanol (i.e., 2-propanol) may find utility in transdermal xanomeline compositions as a component of the formulation. To the extent that such formulation exhibits the characteristics of the present compositions, such formulations are considered to fall within the scope of the present invention.

The present invention provides a transdermal xanomeline patch formulation comprising an effective amount of xanomeline, from 0.1 to 10 parts by weight azone, from 30 to 69.8 parts ethanol, 29 to 50 parts by weight water, from 0 to 30 parts by weight propylene glycol, and 1 to 5 parts by weight Klucel HF. Preferred ranges for the formulation include from 2 to 4 parts by weight azone, from 30 to 55 parts by weight ethanol, from 0 to 20 parts by weight propylene glycol, from 35 to 45 parts water, and from 2.5 to 3.5 parts Klucel HF. One preferred embodiment is to omit propylene glycol from the formulation.

There is provided a transdermal formulation patch wherein an effective amount of xanomeline is intimately distributed in a matrix. One such preferred matrix is a pressure sensitive adhesive.

Further, there is provided a transdermal xanomeline patch formulation comprising an effective amount of xanomeline and from about 50 to 99.9% by weight acrylic adhesive. A preferred range of acrylic adhesive comprises from about 65 to about 99.8% by weight acrylic adhesive. A further preferred range of acrylic adhesive comprises from about 70 to about 98% by weight acrylic adhesive. Another preferred range for the acrylate adhesive is from about 80 to 98 parts by weight. The acrylate adhesive is commercially available and may be purchased for example, from the National Starch and Chemical Corporation, Bridgewater, N.J. 08807, catalog number 80-1054. The acrylate adhesive typically contains 48% solids in 33% ethyl acetate/28% heptane/34% isopropanol/5% toluene by weight.

Additionally, there is provided a transdermal xanomeline patch formulation comprising an effective amount of xanomeline, from 85 to 97 parts by weight ethanol and from 2 to 14.9 parts Klucel HF. Klucel HF is a commercially available gelling agent. For example, Klucel HF may be purchased from Aqualon. Other appropriate gelling agents can be selected by the skilled artisan. Preferred ranges for the formulation are 92 to 96 parts by weight ethanol and 2.5 to 3.5 parts Klucel HF or other appropriate gelling agent. Another preferred range for such formulations comprises from about 93 to about 95 parts by weight ethanol and from about 3 to about 3.5 parts gelling agent.

The compound xanomeline can be prepared as described in U.S. Pat. No. 5,043,345 Sauerberg et. al. ('345) which is hereby incorporated by reference in its entirety. As disclosed in the '345 patent xanomeline can be useful for the treatment of Alzheimer's disease, severe painful conditions, glaucoma, and for the stimulation of cognitive function of the forebrain and hippocampus of mammals.

Xanomeline tablet formulation has been administered to mild and moderately severe Alzheimer's Disease patients. Such tablet formulation of xanomeline was associated with undesired parasympathomimetic effects when administered to a group of subjects. Surprisingly, the presently claimed transdermal formulations of xanomeline can minimize or eliminate such effects while maintaining a consistent, desirable plasma concentration of the pharmacologically active agent.

This invention provides a method for treating a condition associated with modulation of a muscarinic receptor with minimal or no parasympathomimetic effects comprising administering xanomeline transdermally. Examples of such conditions associated with modulation of a muscarinic receptor include, but are not in any way limited to decreased cognition, Alzheimer's Disease, and severe painful conditions. Preferred transdermal patch formulations include but are not limited to a patch formulation comprising an effective amount of xanomeline, azone, ethanol, water, optionally propylene glycol and Klucel HF; an effective amount of xanomeline intimately distributed in a matrix; an effective amount of xanomeline and an acrylic adhesive; an effective amount of xanomeline, ethanol, and Klucel HF; described herein.

As reported herein, plasma levels were determined using gas chromatography methods familiar to the skilled artisan. The artisan can establish the appropriate conditions for the gas chromatographic analysis; however, one set of suggested conditions include the following:

A 30 cm ×0.25 $\mu$m capillary column (J & W Scientific for example); hydrogen flow rate of 3.2 ml/min, helium flow rate of 14.3 ml/min, and air flow of 115.0 ml/min. The gradient column temperature is suggested to be 90 to 270° C., detector at 250° C., and injector at 250° C. A suggested detection type is nitrogen-phosphorus. The artisan will recognize that other conditions will be effective as well; however, the present conditions are provided as guidance to assist the artisan in choosing the most desired parameters for the present conditions.

Suitable enhancers may be additionally be alcohols like 1,2 propane diol, 1,3 butylene glycol, 1-hexadecanol, 2-hydroxy fatty alcohols, 2-octyldodecanol, 2-propanol, benzyl alcohol, cetylstearyl alcohol, diethylene glycol, dipropylene glycol, dodecanol, ethanol, glycerol, hexanediol, octanol, oleyl alcohol, panthenol, phenylcthanol, polyethylene glycols, or polypropylene glycols, or fatty acids like capric acid, linoleic acid, lauric acid, myristic acid, n-valerianic acid, pelargonic acid, also other physiologically acceptable low molecular acids like e.g. 3-phenylpropionic acid, acetic acid, adipic acid, benzoic acid, salicyclic acid or their skin compatible salts.

Similarly, sulphates and sulphonates of fatty acids, like sodium cetylstearyl sulphate sodium lauryl sulphate may be used advantageously. Esters of the formula $[CH_3(CH_2)_mCOO]_nR$, in which m is an integer from 8 to 16, preferably from 8 to 12; n is 1 or 2, preferably 1 and R is a lower alkyl ($C_1$ to $C_3$ residue but also compounds like 1.3 diacetin, capric/caprylic triglyceride, diisopropyl adipate, ethyl oleate, ethylene glycol (di-)stearate, ethylene glycol monostearate, glycerol hydroxystearate, glycerol monostearate, hydrogenated castor oil, oleic acid esters, triacetin, alsophthalate esters like diethyl phthalate or, di-(2-ethylhexyl)-phthalate may be added to the composition.

Other compounds with an advantageous action on the drug substance skin flow include sulfoxides, e.g. dimethyl sulfoxide or dodecylmethyl sulfoxide, amides like diethyl-m-toluamide, dimethyl formamide, fatty acid diethanolamide, $N_2N$ dimethyl acetamide, amines like diethanolamine or triethanolamine, ethylene glycol derivatives like ethoxylated castor oil, oleylalcohol/PEG-5-ether, glycerol ethers with polyethylene glycol, diethylenglycol monomethylether, diethylenglycol monoethylether, terpenes and terpenoids like menthol, thymol, cineol, isobornyl acetate, limonene and finally further compounds not belonging to a specific chemical defined group but known to those skilled in the art to be used for that purpose, e.g. dimethicon, squalen, dimethyl isosorbide, lecithine, glycofurol, urea, N-methyl pyrrolidone.

Acrylic Copolymers

Acrylic copolymers are understood to be more specifically copolymers prepared from esters of acrylic acid and methacrylic acid with $C_1$ to $C_{18}$ alcohols, dimethylaminoethanol or other suitable alcoholic components, vinyl acetate, vinyl pyrrolidone, styrene, butadiene, acryl nitrile or other suitable compounds with a vinyl group.

The following examples are provided to more fully illustrate the invention claimed herein. The examples are provided for illustrative purposes only and are not intended to limit the scope of the invention in any way.

EXAMPLE 1

Transdermal formulation Free Base

A 0.5 g sample of xanomeline free base was dissolved in 9.25 g of ethanol (200 proof). A 0.75 g sample of azone and a 5.0 g aliquot of propylene glycol were added to the ethanol mixture with stirring. A 10 g sample of water was added to the mixture. The mixture was a cloudy suspension. Finally, 0.75 g of Klucel was added to the mixture and stirred until the Klucel was dispersed. The mixture was allowed to stand for 24 hours. A 2.0 g sample of the formulation prepared as described herein was dispensed by syringe into a reservoir-type transdermal adhesive system.

| Time hours post application | Concentration in Dog ng/ml Plasma | | | |
|---|---|---|---|---|
| | 1 | 2 | 3 | Mean + SEM |
| 0 | 0 | 0 | 0 | 0 ± 0 |
| 3 | 19 | 11 | 10 | 10.7 ± 6.0 |
| 6 | 27 | 16 | 16 | 19.7 ± 4.5 |
| 9 | 26 | 17 | 15 | 19.3 ± 4.2 |
| 12 | 16 | 13 | 14 | 14.3 ± 1.1 |
| 15 | 12 | 10 | 12 | 11.3 ± 0.8 |
| 24 | 7 | 8 | 10 | 8.3 ± 1.1 |
| 28 | 6 | 8 | 9 | 7.7 ± 1.1 |
| 32 | 4 | 7 | 8 | 6.3 ± 1.5 |
| 48 | 3 | 6 | 8 | 5.7 ± 1.8 |
| 54 | 0 | 4 | 5 | 3.0 ± 1.8 |
| 72 | 0 | 0 | 0 | 0 ± 0 |

EXAMPLE 2

Transdermal Formulation without Polyethylene Glycol

A 0.5 g sample of xanomeline free base was dissolved in 13.0 g of ethanol (200 proof). A 0.75 g sample of azone was added to the ethanol mixture with stirring. An 11.25 g sample of water was added to the mixture. The mixture was a clear solution. Finally, 0.75 g of Klucel was added to the mixture and stirred until the Klucel was dispersed. The mixture was allowed to stand for 24 hours. A 2.0 g sample of the formulation prepared as described herein was dispensed by syringe into a reservoir-type transdermal adhesive system.

| Time hours post application | Concentration in Dog ng/ml Plasma | | | |
|---|---|---|---|---|
| | 1 | 2 | 3 | Mean + SEM |
| 0 | 0 | 0 | 0 | 0 ± 0 |
| 3 | 19 | 12 | 4 | 11.7 ± 5.3 |
| 6 | 24 | 17 | 6 | 15.7 ± 6.4 |
| 9 | 18 | 11 | 4 | 11.0 ± 4.9 |
| 12 | 12 | 9 | 5 | 8.7 ± 2.5 |
| 15 | 9 | 8 | 3 | 6.7 ± 2.3 |
| 24 | 6 | 5 | 3 | 4.7 ± 1.1 |
| 28 | 9 | 4 | 0 | 4.3 ± 3.2 |
| 32 | 7 | 3 | 0 | 3.3 ± 2.5 |
| 48 | 3 | 0 | 3 | 2.0 ± 1.2 |
| 54 | 0 | 0 | 0 | 0 ± 0 |
| 72 | 0 | 0 | 0 | 0 ± 0 |

| Time hours post application | Concentration in Monkey ng/ml Plasma | | | |
|---|---|---|---|---|
| | 1 | 2 | 3 | Mean + SEM |
| 0 | 0 | 0 | 0 | 0 ± 0 |
| 3 | 50 | 59 | 65 | 58 ± 5.3 |
| 6 | 44 | 50 | 59 | 51 ± 5.3 |
| 8 | 39 | 45 | 45 | 43 ± 2.5 |
| 12 | 25 | 42 | 41 | 36 ± 6.7 |
| 15 | 25 | 34 | 37 | 22 ± 11.8 |
| 24 | 14 | 13 | 16 | 14.3 ± 1.1 |
| 28 | 12 | 8 | 8 | 9.3 ± 1.6 |
| 32 | 9 | 7 | 7 | 7.7 ± 0.8 |
| 48 | 5 | 5 | 4 | 4.7 ± 0.4 |
| 54 | 2 | 2 | 2 | 2 ± 0 |
| 72 | 0 | 0 | 0 | 0 ± 0 |

Patches were applied to the shaved chest of each rhesus monkey.

EXAMPLE 3

Transdermal Xanomeline in Gel

A 1.0 g sample of xanomeline free base was dissolved in 47.5 g of ethanol (200-proof). Then a 1.5 g sample of Klucel gelling agent was added to the solution and stirred until dispersed. The gel was allowed to stand for 24 hours. A 2.0 g sample of the formulation prepared as such was dispensed by syringe into a reservoir-type transdermal adhesive system.

The patches prepared as stated herein were applied to rats. The rats were killed in pairs at various time points after application and the rat brains were removed and frozen. The binding of the M1 antagonist ligand, $^3$H-pirenzepine, to muscarinic receptors in the brain was determined. The decrease in binding is indicative of drug or active metabolite present in the brain. The effect of the drug after oral administration lasts less than 6 hours. The percent of control ex vivo pirenzepine binding at 6 hours was 33%, at 12 hours 15%, at 24 hours 26%, and at 48 hours 53%. The mean plasma concentration using this patch formulation was as follows:

| Time | Mean Plasma Concentration (ng/ml) ± SEM |
|---|---|
| 6 | 109.8 ± 35.53 |
| 12 | 152.4 ± 30.18 |
| 24 | 115.9 ± 43.02 |
| 48 | 28.07 ± 5.995 |

EXAMPLE 4

Transdermal Xanomeline in Acrylic Adhesive

A 600 mg sample of xanomeline free base was dissolved in 41.6 g of pressure sensitive acrylic adhesive (cat. number 80-1054, National Starch and Chemical Corporation, Bridgewater, N.J. 08807). The mixture was agitated for 2 hours on a three roller mill. The mixture was coated along the length of a 3 mil thick release liner using a knife coater providing a 20 mil gap. The 20 mil gap provides an effective 20 mil thick coating of the formulation on the release liner. The sample was allowed to air dry for 24 hours. The sample was laminated on polyester backing.

The patches prepared as stated herein were applied to rats. The rats were killed in pairs at various time points after application and the rat brains were removed and frozen. The binding of the M1 antagonist ligand, $^3$H-pirenzepine, to muscarinic receptors in the brain was determined. The decrease in binding is indicative of drug or active metabolite present in the brain. The effect of the drug after oral administration lasts less than 6 hours. The percent of control ex vivo pirenzepine binding at 6 hours was 101%, at 12 hours 89%, at 24 hours 75%, and at 48 hours 105%.

A transdermal xanomeline patch formulation in acrylic adhesive was prepared substantially as described supra; however, the patch formulation comprised 10.8 g xanomeline per $m^2$ (18% by weight) and 60 g of acrylic adhesive per $m^2$ (82% by weight). Individual 25 $cm^2$ patches were prepared to provide 27.2 mg of xanomeline free base per patch. The patches were applied to the shaved abdomen of rats and the shaved chest of monkeys. The patches were removed at 24 hours.

| | Mean Plasma Concentration in Rat | |
|---|---|---|
| Time | (ng/ml) ± SEM | N– |
| 1.00 | 4.635 ± 1.750 | 3 |
| 2.00 | 7.198 ± 0.986 | 3 |
| 4.00 | 11.211 ± 0.883 | 3 |
| 6.00 | 10.398 ± 1.251 | 3 |
| 8.00 | 8.261 ± 1.193 | 3 |
| 10.00 | 9.576 ± 0.000 | 1 |
| 15.00 | 12.284 ± 3.107 | 3 |
| 18.00 | 9.435 ± 1.540 | 3 |
| 24.00 | 10.870 ± 0.319 | 3 |
| 30.00 | 0.522 + 0.268 | 3 |

Two such adhesive patches were applied to the shaved chest of each monkey. The patches were removed at 24 hours.

| | Mean Plasma Concentration in Monkey | |
|---|---|---|
| Time | (ng/ml) ± SEM | N |
| 1.50 | 25.750 ± 2.160 | 3 |
| 3.00 | 35.467 ± 1.840 | 3 |
| 6.00 | 31.070 ± 2.352 | 3 |
| 9.00 | 31.300 ± 1.578 | 3 |
| 12.00 | 30.230 ± 3.413 | 3 |
| 24.00 | 27.037 ± 1.868 | 3 |
| 28.00 | 8.917 ± 3.301 | 3 |
| 32.00 | 4.867 ± 2.622 | 3 |
| 48.00 | 1.080 ± 0.571 | 3 |

One such adhesive patch was applied to the chest of each monkey. The patches were removed at 24 hours.

| | Mean Plasma Concentration in Monkey | |
|---|---|---|
| Time | (ng/ml) ± SEM | N |
| 1.50 | 69.40 ± 0.205 | 3 |
| 3.00 | 9.897 ± 1.642 | 3 |
| 6.00 | 9.757 ± 0.802 | 3 |
| 9.00 | 9.433 ± 1.140 | 3 |
| 12.00 | 9.760 ± 1.160 | 3 |
| 24.00 | 9.330 ± 0.589 | 3 |
| 28.00 | 1.793 ± 0.101 | 3 |
| 32.00 | 0.800 ± 0.055 | 3 |
| 48.00 | 0.123 ± 0.072 | 3 |

EXAMPLE 5

Transdermal Xanomeline in Acrylic Adhesive 9.0 g Xanomeline free base are dissolved in 91 g of an acrylic adhesive solution (solids content 50.0%, cat. number 901-1052, National Starch & Chemical, Zutphen, The Netherlands). The mixture is stirred for at least 0.5 hours and is coated on a 4 mil siliconized polyethylene terephthalate release liner to provide a coated layer of 60 $g/m^2$ (based on dried matter). The wet layer is dried for 30 minutes at room temperature, then for 10 minutes at 50° C. The sample was laminated on a 1-mil-backing layer of polyetylene terephthalate.

Test samples of approximately 5 $cm^2$ are punched for in vitro skin permeation experiments on pig ear full thickness skin (Franz type diffusion cell, at 37° C.; phosphate buffer pH 4.4 as receptor fluid). A mean (n=3) cumulative permeated amount of 46 $\mu$g Xanomeline was found after 24 hours.

EXAMPLE 6

Transdermal Xanomeline in Acrylic Adhesive 14.3 g Xanomeline free base are dissolved in 85.7 g of an acrylic adhesive solution (solids content 50.0%, cat. number 901-1052, National Starch & Chemical, Zutphen, The Netherlands).

The mixture is stirred for at least 0.5 hours and is coated on a 4 mil siliconized polyethylene terephthalate release liner to provide a coated layer of 60 $g/m^2$ (based on dried matter). The wet layer is dried for 30 minutes at room temperature, then for 10 minutes at 50° C. The sample was laminated on a 1-mil-backing layer of polyethylene terephthalate.

Test samples of approximately 5 $cm^2$ are punched for in vitro skin permeation experiments on pig ear full thickness skin (Franz type diffusion cell, at 37° C.; phosphate buffer pH 5.5 as receptor fluid). A mean (n=3) cumulative permeated amount of 102 μg Xanomeline was found after 24 hours.

EXAMPLE 7

Transdermal Xanomeline in Acrylic Adhesive 18.0 g Xanomeline free base are dissolved in 82 g of an acrylic adhesive solution (solids content 50.0%, cat. number 901-1052, National Starch & Chemical, Zutphen, The Netherlands).

The mixture is stirred for at least 0.5 hours and is coated on a 4 mil siliconized polyethylene terephthalate release liner to provide a coated layer of 60 g/m$^2$ (based on dried matter). The wet layer is dried for 30 minutes at room temperature, then for 10 minutes at 50° C. The sample was laminated on a 1-mil-backing layer of polymethacrylic copolymer.

Test samples of approximately 5 cm$^2$ are punched for in vitro skin permeation experiments on pig ear full thickness skin (Franz type diffusion cell, at 37° C.; phosphate buffer pH 5.5 as receptor fluid). A mean (n=2) cumulative permeated amount of 332 μg Xanomeline was found after 24 hours.

Examples 5 to 7 illustrate the dependence of xanomeline permeation rate on the concentration of the drug.

According to Fick's law, one would expect a linear increase in diffusion (and permeation) rate with increasing drug concentration. However, the following results based on the examples show an unexpected increase.

| Xanomeline Concentration in dry adhesive matrix (% w/w) | Permeated after 24 hours pg/cm$^2$ |
|---|---|
| 18 | 46 (Example 5) |
| 28.5 | 102 (Example 6) |
| 36 | 332 (Example 7) |

The values had been derived from clear solutions of the drug in the adhesive. Unfortunately, the saturation limit of about 23–28% (w/w) in this polymer limits the utilization of this unexpected advantage of highly enriched xanomeline preparations. It is concluded from this unexpected results that an optimum formulation has to contain a slightly subsaturated, saturated or even supersaturated amount of xanomeline for best performance.

We claim:

1. A transdermal patch prepared using a formulation comprising from about 0.1 to 10 parts by weight azone, from about 30 to 69.8 parts ethanol, from about 29 to 50 parts by weight water, from about 1 to 5 parts by weight gelling agent, and an amount of xanomeline that is effective for treating a condition associated with modulation of a muscarinic receptor.

2. A transdermal patch of claim 1, wherein the formulation contains up to 30 parts by weight propylene glycol.

3. A transdermal patch comprising a pressure-sensitive adhesive matrix and an amount of xanomeline that is effective for treating a condition associated with modulation of a muscarinic receptor.

4. A transdermal patch of claim 3, wherein the pressure-sensitive adhesive is selected from the group consisting of polymers and copolymers of alkyl esters of acrylic acid and methacrylic acid, the alkyl group having from 1 to 18 carbon atoms, copolymers of vinyl acetate with ethylene or with any of said acrylic and methacrylic esters, polyvinylpyrrolidone and copolymers of vinyl pyrrolidone, vinyl acetate or with any of said acrylic and methacrylic esters.

5. A transdermal patch of claim 3, wherein the pressure-sensitive adhesive is an acrylic adhesive.

6. A transdermal patch of claim 5 wherein the matrix contains from about 50 to 99.9% by weight acrylic adhesive.

7. A transdermal patch of claim 6 wherein the matrix contains from about 65 to 99.8% acrylic adhesive.

8. A transdermal patch of claim 6 wherein the matrix contains from about 70 to 99.8% acrylic adhesive.

9. A transdermal patch of claim 6 wherein the matrix contains from about 88 to 99.8% acrylic adhesive.

10. A transdermal patch of claim 6 wherein the patch contains from about 80–98% acrylic adhesive.

11. A transdermal patch of claim 3 wherein the condition is Alzheimer's disease.

12. A transdermal patch of claim 3 wherein the condition is decreased cognition.

13. A transdermal patch of claim 3 wherein the condition is a severe painful condition.

14. A transdermal patch prepared using a formulation comprising from about 80 to 97 parts by weight ethanol, from about 2 to 20 parts by weight gelling agent and an amount of xanomeline that is effective for treating a condition associated with modulation of a muscarinic receptor.

15. A transdermal patch of claim 14 wherein the formulation comprises from about 92 to 96 parts by weight ethanol and about 2.5 to 3.5 parts by weight gelling agent.

16. A transdermal patch of claim 14 wherein the formulation comprises from about 85 to 97 parts by weight ethanol and from about 2 to 15 parts by weight gelling agent.

17. A method for treating a condition associated with modulation of a muscarinic receptor comprising administering xanomeline transdermally using a patch of claim 3.

18. A method of claim 17 wherein the condition is decreased cognition.

19. A method of claim 17 wherein the condition is Alzheimer's disease.

20. A method for treating a condition associated with modulation of a muscarinic receptor comprising administering xanomeline using a transdermal patch of claim 8.

* * * * *